United States Patent [19]

Karbach et al.

[11] Patent Number: 5,437,187

[45] Date of Patent: Aug. 1, 1995

[54] ULTRASOUND TEST APPARATUS FOR ELONGATED TEST SPECIMENS HAVING CROSS SECTIONS THAT ARE CONSTANT THROUGHOUT THEIR LENGTH, IN PARTICULAR PIPES AND RODS

[75] Inventors: Bernhard Karbach, Erftstadt-Friesheim; Ottokar Patzke, Erftstadt-Liblar; Reinhard Prause, Sankt Augustin, all of Germany

[73] Assignee: Firma Krautkramer GmbH & Co., Germany

[21] Appl. No.: 96,486

[22] Filed: Jul. 22, 1993

[30] Foreign Application Priority Data

Jul. 24, 1992 [DE] Germany .................. 42 24 538.9

[51] Int. Cl.$^6$ ...................... G01N 29/00; G01N 29/26
[52] U.S. Cl. ................................. 73/635; 73/622
[58] Field of Search ............... 73/635, 620, 622, 628, 73/644

[56] References Cited

U.S. PATENT DOCUMENTS

| | | | |
|---|---|---|---|
| 3,375,706 | 4/1968 | Pondelis et al. | 73/644 |
| 3,472,064 | 10/1969 | Kortenhoven | 73/644 |
| 3,561,258 | 2/1971 | Ashford | 73/622 |
| 3,777,554 | 12/1973 | Papay et al. | 73/644 |
| 4,562,738 | 1/1986 | Nakayama et al. | 73/622 |
| 4,596,953 | 6/1986 | Nagasaka et al. | 73/622 |
| 4,718,277 | 1/1988 | Glascock | 73/622 |
| 5,007,291 | 4/1991 | Walters et al. | 73/622 |
| 5,016,475 | 5/1991 | Aburatani et al. | 73/644 |
| 5,088,328 | 2/1992 | John, Jr. et al. | 73/622 |
| 5,174,155 | 12/1992 | Sugimoto | 73/622 |
| 5,178,014 | 1/1993 | John, Jr. et al. | 73/622 |
| 5,313,837 | 5/1994 | Haynes | 73/622 |
| 5,335,546 | 8/1994 | Karbach et al. | 73/622 |

FOREIGN PATENT DOCUMENTS

| | | | |
|---|---|---|---|
| 2308208 | 9/1974 | Germany | 73/635 |
| 3837144 | 5/1990 | Germany | 73/622 |
| 4040870 | 6/1992 | Germany | 73/622 |
| 2027199 | 2/1980 | United Kingdom | 73/622 |
| 563620 | 6/1977 | U.S.S.R. | 73/622 |
| 832463 | 5/1981 | U.S.S.R. | 73/622 |

Primary Examiner—Thomas P. Noland
Assistant Examiner—Daniel S. Larkin
Attorney, Agent, or Firm—Quarles & Brady

[57] ABSTRACT

Along with an ultrasound test apparatus for elongated test specimens (20) having cross sections that are constant throughout their length, in particular pipes and rods, which pass longitudinally along a test line (24) and thereby pass through a test machine (28) which is arranged on the test line (24), a second test machine (34) is provided. Both test machines (28, 34) are arranged on a pivot mount (30) at some distance from each other, parallel to each other and rotated 180° with respect to each other, rotatable by at least 180° around an axis of rotation (38), the axis of rotation running at a right angle to the test line (24) and at some distance from it, so that in an initial rotation position of the pivot mount (30) the one test machine (28) is positioned on the test line (24) and the other test machine (34) can be changed over, and in the second rotation position the other test machine (34) is positioned on the test line (24) and the first test machine (28) can be changed over.

20 Claims, 2 Drawing Sheets

ULTRASOUND TEST APPARATUS FOR ELONGATED TEST SPECIMENS HAVING CROSS SECTIONS THAT ARE CONSTANT THROUGHOUT THEIR LENGTH, IN PARTICULAR PIPES AND RODS

BACKGROUND OF THE INVENTION

The invention relates to an ultrasound test apparatus for elongated test specimens that are constant throughout their length, in particular pipes and rods that are transported longitudinally along a test line and thereby pass through a test machine that is arranged on the test line.

So called whole body test installations are used as test machines for test specimens having a round, outer cross section or a regular, polygonal profile, the test specimens are scanned along a helical path with ultrasound. The test specimens are moved along the test line relative to the test machine. Either the test specimens are themselves additionally rotated around their longitudinal axis with the test machine remaining fixed, or the test machine has a rotor which turns around the axis of the test specimen, that is, the test line. Such test installations are, for example, described in J and H Krautkrämer, "Ultrasonic Testing of Materials," 4th revised edition, Translation of 5th German Edition, Springer Verlag, pages 442 to 461.

However, other longitudinal profiles may be considered as test specimens, for example fin wing pipes, train tracks, ingots, special profiles or the like. With such test specimens helical scanning, in general, is not possible. Ultrasound testing is thus carried out through multiple, locally fixed test heads on a test machine. The test heads are arranged along the outer contour of the profile such that the necessary, user selected tests can be run.

Ultrasound test devices of the type mentioned above are, as a rule, adjusted by the manufacturer of the test pieces, in conjunction with production. The ultrasound test should, however, on the one hand yield the maximal possible result with respect to the quality of the individual test specimens but, on the other hand, not delay production or make it more difficult.

During production a certain tonnage of test specimens with a pregiven cross section form are typically produced first, and then a second type of profile form is processed, etc. In order to carry out such a change in profile an ultrasound test device must be adapted relatively rapidly, in any case quickly enough so that production of the profiled parts is not delayed. Accordingly, there have been attempts to make the ultrasound test apparatus change over quickly from one profile form to another profile form. These solutions, however, have not kept pace with modern developments in production.

SUMMARY OF THE INVENTION

Using this as a starting point, it is the task of the invention to further-develop an ultrasound test apparatus of the above mentioned type, so that the most rapid possible change over from one profile type to another profile type can occur without having production effected to an appreciable extent by the change over of the ultrasound test apparatus.

Starting from the ultrasound test device of the type indicated above, this task is accomplished in that a second test machine is provided, that the two test machines are arranged on one rotating rack at some distance from each other, parallel to each other and rotated 180° with respect to each other, that a rotation of at least 180° occurs around one rotational axis that is perpendicular to the test line and runs at some distance from this, so that at an initial rotating position of the pivot mount one test machine is positioned on the test line and the other test machine can be changed over, while in the second rotational position the other test machine is positioned on the test line and the first test machine can be changed over.

The invention thus recommends providing two separate, independently utilizable test devices that can be arranged together on a pivot mount. During practical operation a test machine is always located on the test line, that is, in the test position, while the other test machine is located in the change over position. One test machine can be serviced, adjusted or changed over while the other test machine can test charges of test pieces having one type of profile shape. When the charge is changed, the other test machine has already been adjusted to the new profile type and, when the new profile type is advanced for testing, it can be rotated into the test position by simply rotating the pivot mount 180° onto the test line. The change over of the ultrasound test apparatus between two profile types can therefore be accomplished in the shortest possible time. Since the two test machines are arranged rotated by 180° on the pivot mount, the direction of passage of the test specimens and the position of the respective turning machines always remains the same in the change over position. This provides the advantage that only one adjustment device, preferably a manipulator for standards, must be provided.

The rotating table extends the test path only insignificantly in the direction of passage. No additional drive and guide stations are required for the test specimens.

The location for the set up and change over is always the same for the test machine that is positioned outside of the test line. The same auxiliary set up means can be used, e.g. a manipulator according to DE 40 40 870 A1, and ultrasound auxiliary electronics to set up the mechanics.

It has been proven to be very advantageous if the outer circular diameter of the pivot mount is as small as possible. Accordingly, only the required test mechanics for both ultrasound test machines are arranged on the pivot mount, while the individual electronics for one or for both test mechanics are located outside of the pivot mount. Moreover, the construction of the test machine is such that the diameter of the pivot mount can remain small, that is, the drive motors are arranged above or below the test mechanics and are not essential mechanical components, such as, for example, water lines and valves, and are arranged above the mechanics.

It has been proven to be very advantageous to connect each of the test mechanics with the pivot mount in a slideable fashion by means of a crossrail. This crossrail permits each of the test mechanics to move transverse to the test line and transverse to the rotational axis between a retracted position and an extended position in which the test mechanics are located on the test line. The ultrasound test apparatus according to the invention can also be utilized where there is too little space for the pivot mount to rotate without such transverse movement. A rotation of the pivot mount can only take place when the two test mechanics are retracted.

It has been proven advantageous to arrange both test mechanics so as to be vertically adjustable on the pivot mount. Furthermore, in an alternate form, it is advantageous for the pivot mount itself to be vertically adjustable. Variable cross section dimensions, in particular pipe diameters, can thereby be tested.

Both test machines can be, but are not required to be, of like construction. It is possible to provide two variable test machines, for example a test machine for small pipe diameters and a test machine for larger pipe diameters.

The ultrasound test apparatus according to the invention includes the advantage that, to change over and adjust a test machine to a new testing assignment there is normally sufficient time available, so that the change over and adjustment can be carried out in a careful manner and can be double checked before the test begins, without time pressure.

BRIEF DESCRIPTION OF THE DRAWINGS

Further advantages and characteristics of the invention are found in the following specification of an exemplified embodiment, which is to be understood as non-limiting and will be explained in more detail with reference to the drawing. Shown are.

BRIEF DESCRIPTION OF THE PREFERRED EMBODIMENTS

Figure 1:
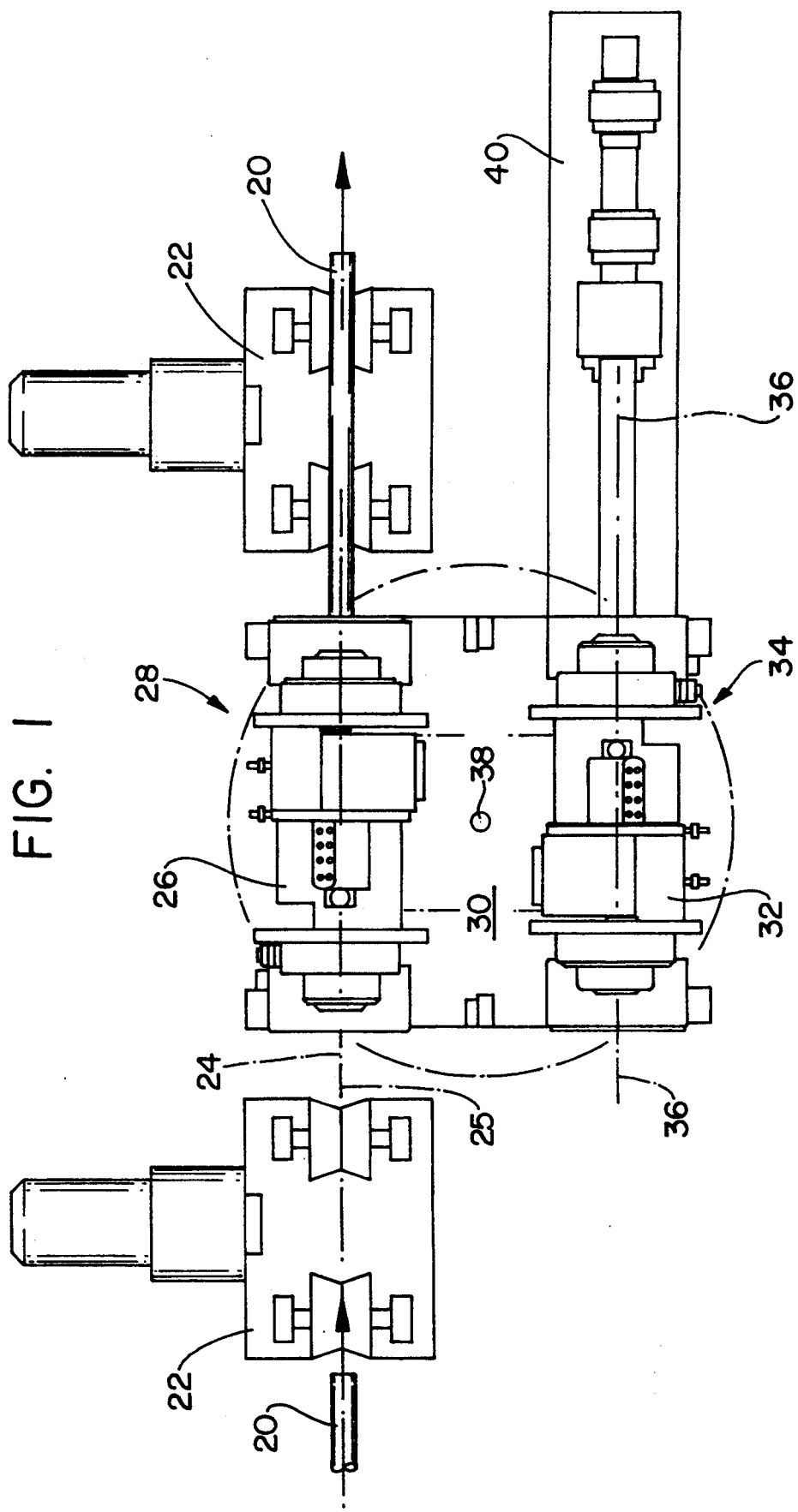
FIG. 1 a top view onto an ultrasound test apparatus according to the invention.

In the illustrated ultrasound test apparatus test specimens 20 are advanced and guided by means of a roller bed 22 along a test line 24. With pipes and round rods the test line 24 coincides with the axis of the pipe or the rod. The test specimens 20 are, as figure i shows in particular, transported in the longitudinal direction.

The first test machine 28 is arranged on a pivot mount 30, on which the test mechanics 32 of a second test machine 34 are also located. In the illustrated, exemplified embodiment both test mechanics 26, 32 are of like construction, but this is not a requirement. The illustrated, exemplified embodiment, furthermore, involves so called rotary test machines, which is also not to be viewed as limiting, while at least one test machine can also be constructed in a different form, for example as a whole-body test installation using a pooling technique as the coupling technique, as is specified, for example, in DE 38 37 144 A1.

Figure 2:
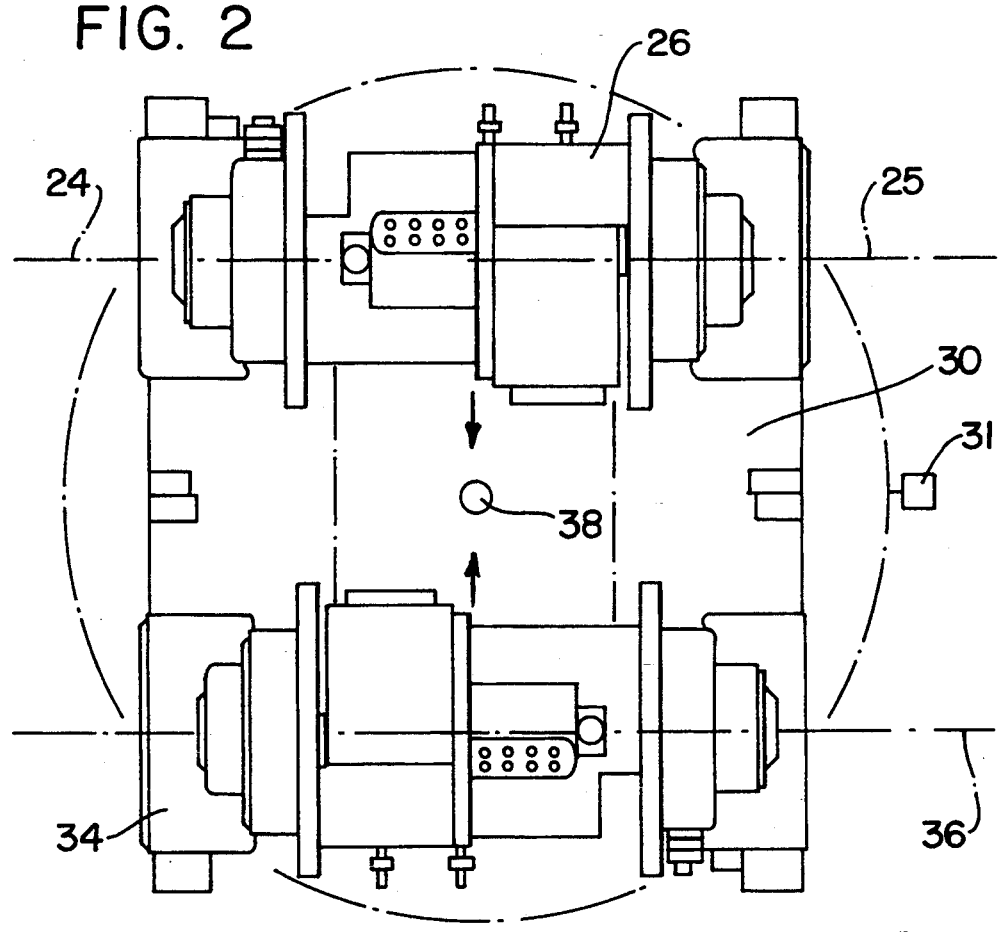
FIG. 2 a top view according to FIG. 1, onto the pivot mount in enlarged illustration and FIG. 3 a lateral view of the arrangement according to FIGS. 1 and 2.

As is shown in particular in FIG. 2, the two test mechanics 26, 32 are arranged with respect to each other such that their machine test lines 25, 36 run in parallel. The machine test line 25 of the first test machine 28, which is located in the test field, obligatorily coincides with the test line 24. The machine test line 36 is the test line of the second test machine 34. Moreover, the two test mechanics 26, 32 are arranged 180° displaced. Finally, both are arranged at the same distance from a rotational axis 38 of the pivot mount 30, specifically stated, their test lines 24, 36 are at the same distance from this rotational axis 38. This distance is selected as small as possible in order to keep the outer diameter of the rotational circle of the overall arrangement as small as possible. For this reason all of the mechanical devices that do not need to be on the test line 24 are arranged above (preferably) or also below the actual test mechanics 26, 32, insofar as they need to be mounted on the pivot mount 30. All mechanical parts which are not lodged there are installed fixed in place. In particular, the electronics 50 illustrated in FIG. 3 are fixed in place and arranged outside of the pivot mount 30.

As is shown in FIG. 1, a manipulator 40 is located on the machine profile line 36 of the second test machine 34, which is in the change over position. The manipulator adjusts the test mechanism 32 of the second test machine 34. A manipulator does not need to be specified separately here, reference is made to DE 40 40 870 A1 and DE 40 21 477 A1, which refer to test piece manipulators, and their disclosed contents are entirely included in the disclosed content of the present application.

Preferably, the pivot mount 30 has a sump arranged underneath the test mechanics 26, 32 or is itself formed as a sump. This sump collects the coupling water. The coupling water is again pumped up from this sump and, possibly following an intermediate washing step, is again Used for coupling.

Figure 3:
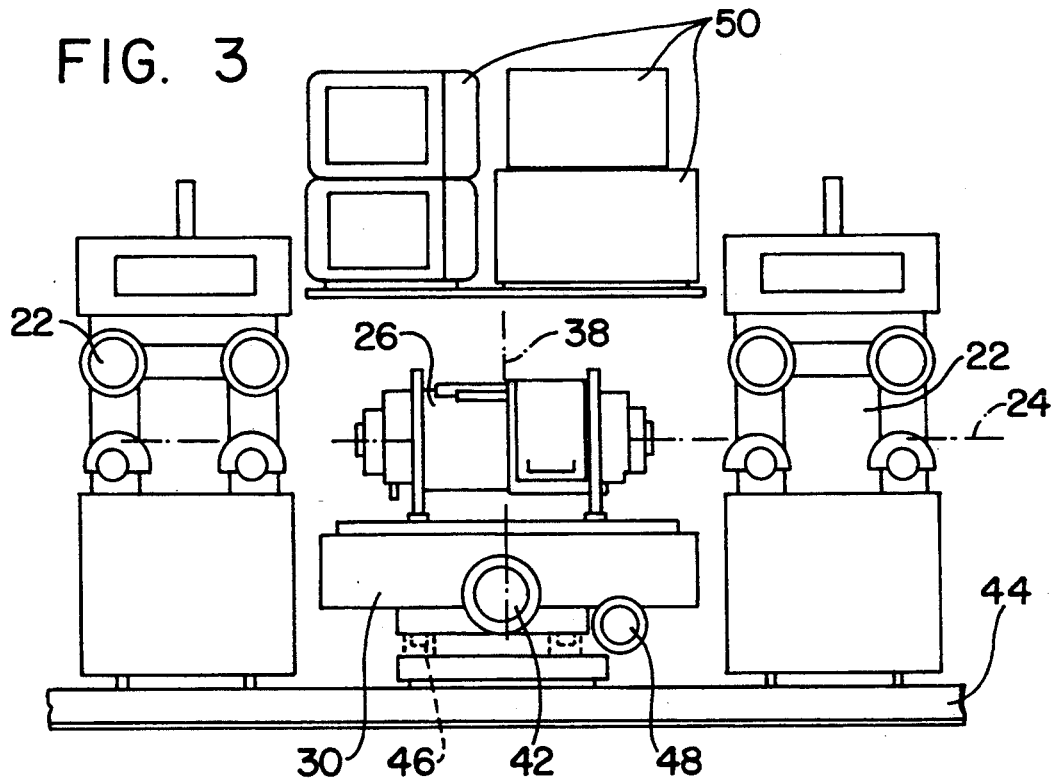

The pivot mount 30 can also be adjusted vertically by means of a manually actuated adjustment device, an adjusting wheel 42 of which is illustrated in FIG. 3. The vertical adjustment takes place with respect to a base 44, on which the roller beds 22 are arranged. As is shown by means of a dot-dashed line in FIG. 3, a crossrail 46 consisting of two parallel rails is provided as an advantageous further development, between the base 44 and the pivot mount 30. On this crossrail 46 the entire pivot mount 30 can be moved perpendicular to the test line 24 and perpendicular to the axis of rotation 30. The rotation of the pivot mount 30 can thereby take place in a position of the crossrail 46 at which the pivot mount 30 is at the greatest distance from the test line 24.

In this way the necessary space for a rotational movement does not need to be provided on the test line 24.

In the illustrated embodiment the pivot mount 30 is rotated by 180°, and a drive wheel 48 is provided for this purpose.

The pivot mount 30 features a fixing means for the terminal rotation positions. Only the test mechanics 26, 32 of the test machines 28, 34 are arranged on the pivot mount 30, and the common electronics 50 of both test machines 28, 34, are arranged next to the pivot mount 30.

We claim:

1. An ultrasound test apparatus for elongated specimens which have constant cross sections along entire lengths of the specimens, in which a specimen passes longitudinally along an axis of a test line and thereby passes through a test position arranged on the test line, said ultrasound test apparatus comprising:

first and second test machines; and a pivot mount rotatable about an axis of rotation which is perpendicular to the axis of the test line and spaced therefrom, said first and second test machines mounted on said pivot mount at different angular positions about the axis of rotation, said pivot mount having a first rotational position at which said first test machine is located at the test position on the test line and the second test machine is located at a changeover position remote from the test line, and having a second rotational position at which the second test machine is located at the test position on the test line and said first test machine is located at a changeover position remote from the test line.

2. The ultrasound test apparatus according to claim 1 wherein said first test machine is mounted 180 degrees around the axis of rotation from said second test machine.

3. The ultrasound test apparatus according to claim 1 further comprising a manipulator which engages said first and second test machines in the changeover position.

4. The ultrasound test apparatus according to claim 3 wherein said first and second machines are arranged so as to be vertically adjustable on said pivot mount.

5. The ultrasound test apparatus according to claim 3 wherein said pivot mount comprises a crossrail on which said first and second machines are slidably mounted for movement transverse to the axis of rotation and transverse to the axis of rotation, wherein either one of said first and second machines in the first rotational position is able to slide along the crossrail between a retracted position and an extended position which corresponds to the test position on the test line.

6. The ultrasound test apparatus according to claim 1 wherein said first and second machines are arranged so as to be vertically adjustable on said pivot mount.

7. The ultrasound test apparatus according to claim 6 wherein said pivot mount comprises a crossrail on which said first and second machines are slideably mounted for movement transverse to the axis of rotation and transverse to the axis of rotation, wherein either one of said first and second machines in the first rotational position is able to slide along the crossrail between a retracted position and an extended position which corresponds to the test position on the test line.

8. The ultrasound test apparatus according to claim 1 wherein said pivot mount comprises a crossrail on which said first and second machines are slideably mounted for movement transverse to the axis of rotation and transverse to the axis of rotation, wherein either one of said first and second machines in the first rotational position is able to slide along the crossrail between a retracted position and an extended position which corresponds to the test position on the test line.

9. The ultrasound test apparatus according to claim 1 further comprising a mechanism for vertically moving said pivot mount.

10. The ultrasound test apparatus according to claim 1 wherein said pivot mount comprises a means for fixing the rotational position of said pivot mount.

11. The ultrasound test apparatus according to claim 1 wherein said pivot mount is slideably connected to a crossrail which extends transverse to the test line and transverse to the axis of rotation thereby enabling said pivot mount to slide transverse to the test line.

12. The ultrasound test apparatus according to claim 1, characterized by the specimens being transported horizontally along the test line and the axis of rotation of the pivot mount being vertical.

13. The ultrasound test apparatus according to claim 12 further comprising a manipulator which engages said first and second test machines in the changeover position.

14. The ultrasound test apparatus according to claim 12 wherein said first and second machines are arranged so as to be vertically adjustable on said pivot mount.

15. The ultrasound test apparatus according to claim 12 wherein said pivot mount comprises a crossrail on which said first and second machines are slideably mounted for movement transverse to the axis of rotation and transverse to the axis of rotation, wherein either one of said first and second machines in the first rotational position is able to slide along the crossrail between a retracted position and an extended position which corresponds to the test position on the test line.

16. The ultrasound test apparatus according to claim 1 characterized by said first and second test machines having test mechanics and electronics with the test mechanics being located on said pivot mount and the electronics are located separate from the pivot mount.

17. The ultrasound test apparatus according to claim 16 wherein the test mechanics of both said first and second test machines share common electronics.

18. The ultrasound test apparatus according to claim 16 further comprising a manipulator which engages said first and second test machines in the changeover position.

19. The ultrasound test apparatus according to claim 16 wherein said first and second machines are arranged so as to be vertically adjustable on said pivot mount.

20. The ultrasound test apparatus according to claim 16 wherein said pivot mount comprises a crossrail on which said first and second machines are slideably mounted for movement transverse to the axis of rotation and transverse to the axis of rotation, wherein either one of said first and second machines in the first rotational position is able to slide along the crossrail between a retracted position and an extended position which corresponds to the test position on the test line.

* * * * *